United States Patent
Dukhovlinov et al.

(10) Patent No.: US 9,480,737 B2
(45) Date of Patent: Nov. 1, 2016

(54) POLYVALENT FUSION PROTEIN VACCINE AGAINST INFLUENZA

(71) Applicant: Universal BioSystems Limited Company (UBS Ltd), Saint-Petersburg (RU)

(72) Inventors: Ilya Vladimirovich Dukhovlinov, St. Petersburg (RU); Anton Iosifovich Orlov, St. Petersburg (RU); Ljudmila Markovna Tsybalova, Saint-Petersburg (RU); Oleg Ivanovich Kiselev, Saint-Petersburg (RU)

(73) Assignee: UNIVERSAL BIOSYSTEMS LIMITED COMPANY (UBS LTD), Saint-Petersburg (RU)

( * ) Notice: Subject to any disclaimer, the term of this patent is extended or adjusted under 35 U.S.C. 154(b) by 0 days.

(21) Appl. No.: 14/768,107

(22) PCT Filed: Feb. 14, 2014

(86) PCT No.: PCT/RU2014/000096
§ 371 (c)(1),
(2) Date: Aug. 14, 2015

(87) PCT Pub. No.: WO2014/126510
PCT Pub. Date: Aug. 21, 2014

(65) Prior Publication Data
US 2015/0374814 A1 Dec. 31, 2015

(30) Foreign Application Priority Data
Feb. 15, 2013 (RU) ................ 2013107777

(51) Int. Cl.
*A61K 39/145* (2006.01)
*C12N 7/00* (2006.01)
*A61K 39/12* (2006.01)
*A61K 39/00* (2006.01)

(52) U.S. Cl.
CPC ............. *A61K 39/145* (2013.01); *A61K 39/12* (2013.01); *C12N 7/00* (2013.01); *A61K 2039/55516* (2013.01); *A61K 2039/55544* (2013.01); *A61K 2039/70* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

2010/0297174 A1  11/2010  Garcia-Sastre et al.
2012/0064117 A1   3/2012  Ross et al.

FOREIGN PATENT DOCUMENTS

RU   2358981 C2   6/2009
WO   0032228 A2   6/2000

OTHER PUBLICATIONS

Fluzone®, 2009-2010 Fluzone Seasonal influenza vaccine package insert, 2009.*
Wang et al., Incorporation of Membrane-Anchored Flagellin into Influenza Virus-Like Particles Enhances the Breadth of Immune Responses, 2008, Journal of Virology, vol. 82, No. 23, pp. 11813-11823.*
International Search Report Application No. PCT/RU2014/000096 Completed: Jul. 1, 2015; Mailing Date: Aug. 14, 2014 2 pages.

* cited by examiner

*Primary Examiner* — Benjamin P Blumel
(74) *Attorney, Agent, or Firm* — The Roy Gross Law Firm, LLC; Roy Gross

(57) ABSTRACT

A vaccine having a fusion protein set forth as SEQ ID NO:1 containing antigenic determinants of haemagglutinins of influenza A and B viruses and flagellin fragments functioning as safe adjuvant, joined via flexible hinges is given, which can be used for prophylaxis of influenza caused by existing influenza A and B strains as well as by possible reassortants. Usage of the vaccine will provide a universal protection against influenza and provides safety, efficacy, polyvalence and preventive effect.

4 Claims, 2 Drawing Sheets

POLYVALENT FUSION PROTEIN VACCINE AGAINST INFLUENZA

FIELD OF THE INVENTION

The embodiment of present invention relates to molecular biology, biotechnology, preparative biochemistry, medicine, and can be used for prophylaxis of influenza, caused by existing influenza strains, as well as by possible reassortants.

BACKGROUND OF THE INVENTION

The term "fusion protein" refers to a protein, obtained by an expression of a recombinant DNA molecule, in which coding arrays of several different genes are bound to one reading frame.

Annually, influenza virus affects from 5 to 15 percent of the population, causing acute respiratory diseases. Every year, vaccines against seasonal influenza are produced and widely used. However, a danger of pandemic spread of certain influenza virus strains with a new combination of genes exists. Such viruses can be more aggressive and cause a higher level of complications and fatalities. In 2009, an unfavorable situation took place, which was connected with an extension of the highly pathogenic influenza virus A(H1N1)pdm/09. Diseases were caused by the influenza virus with new antigenic determinants. In particular, specialists were worried about the fact that the new virus was a reassortant of viruses, circulating among both animals (swine) and humans. According to WHO, the infection ratio for humans, who had contact with contracted people, was 22% to 33% for A(H1N1) pdm/09. In comparison, the analog ratio for a seasonal influenza ranges from 5% to 15%.

The viral surface protein haemagglutinin (HA) is of particular interest in the light of development of the vaccines. HA is responsible for virus binding to cell receptors and in such a way for susceptibility to the disease. Mutations of HA usually lead to the increase of epidemiological and sometimes pandemic viral potential.

B-cell and T-cell response is being developed against antigenic determinants of viral proteins—the epitopes. Immunization against viral infections, namely influenza virus, based on usage of amino acid sequences represented by the viral epitopes, show great promise for the development of immune response against the virus and allows to create a universal vaccine for the prevention of both seasonal infection episodes and pandemic. Usage of antigenic determinants of different viral subtypes in one construct makes the production of the polyvalent vaccine easier and allows to create effective vaccines against new viral strains.

It is essential to create a universal vaccine, which would be able to provide defense against the existing and possible reassortant influenza virus strains. The usage of vaccines, based on recombinant proteins, allows to avoid risks, which are connected even with the injection of inactivated viruses. A number of attempts has been made recently to create such a universal safe vaccine.

There is an invention, according to which the gene, coding for a multiepitopic haemagglutinin of the avian influenza virus, is used within the vector construct for the production of the recombinant multiepitopic vaccine in plants (RU 2008139004 A, Oct. 1, 2008). In the patent applications US 2009106864 (2009) and RU 2008139004 the authors used the consensus sequence of the avian influenza A virus haemagglutinin, codon optimized for the expression in plants. In the patent application JP2009102416 (2009) the authors used baculovirus constructs in the insect cells for the expression of haemagglutinin of influenza A and B viruses. The disadvantage of such approaches is the usage of protein (haemagglutinin) sequence from only one influenza virus subtype (H5N1). This narrows the spectrum of the vaccine activity. Moreover, the expression in plants and insect cells provides lower protein yields in comparison to the expression in E. coli.

Several fusion polypeptides are known which include a sequence with a high percentage of homology with the superficial HA-protein of the influenza A virus, containing five immunodominant antigenic epitopes (RU 92004487, Dec. 10, 1992). One of the suggested applications for such polypeptides is to provide vaccines against corresponding antigens, for treatment and prophylaxis (including immunotherapeutic methods) in case of infection by such antigens. However, it is not specified, haemagglutinin of which subtypes is used. In the course of the development of the universal vaccine, the antigenic determinants of haemagglutinin of the influenza B virus as well should be taken into consideration, because the immunogenicity of the vaccine is limited by the strains, the sequences of which are used.

A polyvalent influenza vaccine is known which contains a polyvalent anti-influenza antigen, an adjuvant, an agent that provides the vaccine penetration, and an acceptable excipient (CN101450209, Dec. 31, 2008). Antigens represented by H1-H16 and N1-N9 are declared as an antigenic component. A polyvalent influenza vaccine is also known consisting of surface viral proteins A/H1N1, A/H3N2, haemagglutinin of the B-type (CN101524538, Mar. 26, 2009), an adjuvant—glycerol or aluminum hydroxide. The usage of both an acceptable adjuvant and antigenic determinants in the fusion construct, as well as using single protein type—haemagglutinin will allow to simplify and reduce the cost for the production of the vaccine, inasmuch as it will be no more necessary to adjust the conditions and to control the quality of the component production.

A polyvalent vaccine is known which is based on the inactivated viruses. The active component is represented by antigens A/H1N1, H3N2, B, H5N1, and A (H1N1)pdm/09 (CN101732711, Dec. 31, 2009). The listed antigens are extracted from the inactivated viruses, which means that the scaled-up production of the vaccine can be limited by possible problems, connected with the usage of viruses, especially influenza viruses. For instance, it is necessary to create appropriate working conditions, to handle easily transmitted highly pathogenic virus strains. Moreover, the listed antigens are separate proteins—the advantages of usage of a fusion construct are listed above.

The prototype of the invention is a mixture of flagella, containing at least four protein epitopes of influenza virus, which interact with human cells, whereat each one is being expressed separately in the flagellin of *Salmonella* (WO0032228, Nov. 30, 1998). The listed epitopes refer to the group consisting of: (i) one haemagglutinin epitope, interacting with B cells, (ii) one epitope of haemagglutinin (HA) or of a nucleoprotein (NP), which can bind to MHC molecules for representation to receptors on the surface of the T helper cells and (iii) at least two nucleoprotein (NP) epitopes or a matrix protein (M) which are restricted by the MHC antigens that dominate by the Caucasians and bind to cytotoxic T lymphocytes (CTL).

In the present invention, flagellin FliC of *Salmonella typhimurium* fulfills an adjuvant function. Due to its interaction with Toll-like receptor-5 (TLR-5), FliC stimulates maturation of macrophages and dendritic cells, which results in induction of the immune response (Mc Dermott P. F. High-affinity interaction between Gram-negative flagellin and a cell surface polypeptide results in human monocyte activation. Infect. Immun.—2000.—V. 68.—p.: 5525-5529; Means T. K. et al. The Toll-like receptor 5 stimulus bacterial flagellin induces maturation and chemokine production in human dendritic cells. J. Immunol.—2003.—V. 170.—p.: 5165-5175).

At the moment, flagellin is one of the most promising and well-studied new-generation adjuvants. The results of studies show that recombinant proteins, inoculated together with flagellin, possess higher immunogenic and antigenic properties. The responses to them are registered in shorter times and induce a more intense cellular and humoral immune response (Balaram, 2008).

The disadvantage of such invention lies in the complexity of the immunizing mixture. The usage of a fused protein, containing B and T cell epitopes of different influenza A and B virus subtypes, and flagellin, will trigger an intense immune response and lower the production costs. Therewithal, it is practical to use only components of flagellin. Two receptor-activating sites were detected in the terminal sites of flagellin (aa 79-117 and aa 08-439) (Tonyia, 2001).

TLR-5 is expressed on the cells of the innate immunity, epithelial, and endothelial cells (Sebastiani G. et al. Cloning and characterization of the murine Toll-like receptor 5 (Tlr5) gene: sequence and mRNA expression studies in *Salmonella*-susceptible MOLF/Eimice. Genomics.—2000. —V. 64.—p. 230-240; Zarember K. A. and Godowski P. J. Tissue expression of human Toll-like receptors and differential regulation of Toll-like receptor mRNAs in leukocytes in response to microbes, their products, and cytokines. J. Immunol.—2002.—V. 168.—p. 554-561; Delneste, 2007). Taking this into consideration, it is practical to use mucosa for immunization, which will make the transport of the immunogen easier.

DESCRIPTION OF THE INVENTION

The present invention embodies a vaccine comprising a fusion protein set forth as SEQ ID NO:1 containing fragments of influenza A virus proteins H1, H3, H5, of influenza B virus haemagglutinin, flagellin components, connected via flexible links, wherein the flagellin components function as adjuvant. The represented protein fragments are conservative regions of haemagglutinins H1, H3, H5, and B. In course of naturally occurring infection, specific antibodies are produced against them, which cross-react with homolog epitopes amongst various strains of the influenza A and B viruses. The usage of the epitopes of several proteins will allow to increase the efficacy of the vaccine, and, due to the flexible hinges that join the epitopes, the correct three-dimensional structure of the protein will be provided, which will facilitate an adequate functioning of each epitope.

According to the chosen amino acid sequence, the appropriate nucleotide sequence set forth as SEQ ID NO:2 was calculated by reference to the occurrence of the codons in the protein-coding genes of *E. coli*; at the same time, the codons were chosen by reference of the decrease of dG of the corresponding mRNA.

The main technical result of usage of the invention is that the valency of the influenza vaccine increases: after introduction of the vaccine claimed in the present invention an immunity is developed against different subtypes of both influenza A and B viruses—against the existing and even against those subtypes that can appear as a result of reassortment of any other influenza virus strains. After the vaccine introduction, antibodies against the epitopes of haemagglutinin from different influenza virus strains are being produced in the body. Thus, an ability to produce antibodies in response to influenza virus infection is being developed. Thereafter, immune response upon the infection with any influenza virus will be developed faster, which will result in avoidance of the infection or the disease will be milder. Such approach will allow to eliminate the present disease.

The technical result of the codon optimization of the nucleotide sequence is in protein yields increase.

Therewithal, usage of flagellin components as a non-toxic adjuvant will increase the immune response, developed to the vaccine.

The technical result is also in lowering the price and speeding up of the vaccine production due to a single component (the fusion protein) production instead of a set of vaccine mixture (the prototype) components.

For production of the fusion protein—of the present invention, standard methods of molecular biology and microbiology can be used, which are familiar to a person having ordinary skill in the art. Such methods are described in scientific literature.

EXAMPLE 1

Modeling of the Fusion Protein

The planned fusion polypeptide is a complex multidomain protein (6 domains: FliC1, FliC2, H1, H3, H5, B). For modeling of the multidomain protein following procedures were performed: estimation of the domain boarders, construction of a model of the full protein for estimation of the domains orientation, construction of models for each domain (using examples of 3D structures and ab initio-based modeling), docking of the models using the model of the full protein.

In the planned fusion polypeptide, two domains possessed prototypes and four thereof needed the ab initio-based modeling; furthermore during the ab initio-based modeling, flexible hinges between domains had to be formed.

For generation of realistic results in automatic mode, an I-Tasser algorithm was used, which had been considered the best in the last three protein-modeling competitions— CASPs (Critical Assessment of protein Structure Prediction). This analysis was being performed for five days. However, even by means of this strong algorithm, the generation of realistic data for the multidomain protein including the ab initio-based modeling of domains and their borders is not fully valid (70%).

For the purpose of generation of more exact data, the protein was split into used domains, and then their modeling was performed, using I-Tasser, followed by their docking.

Figure 1:
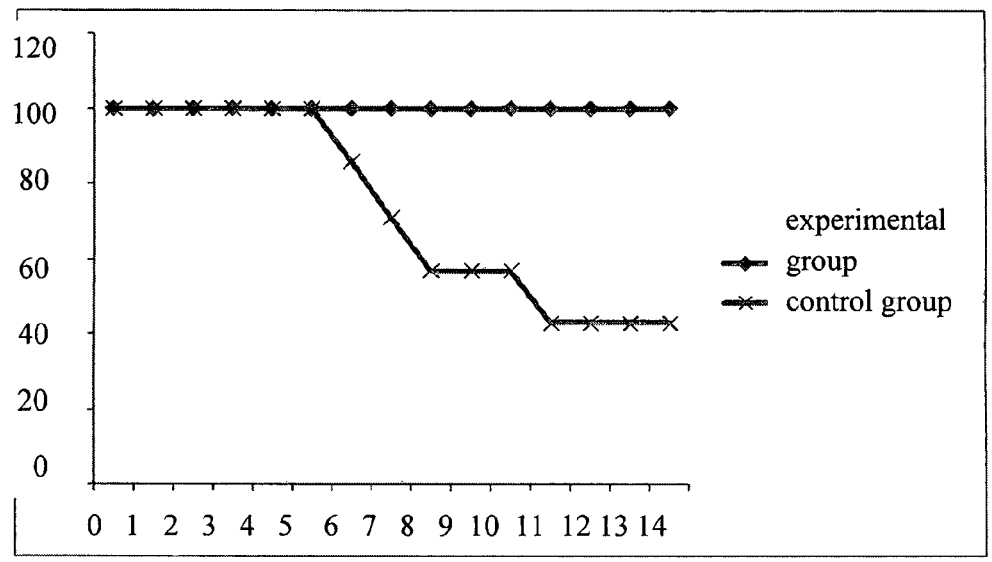
FIG. 1. Dynamics of mice survival rate after infection with 1 LD/50 of virus A/PR/8/34 (H1N1). The days post infection are displayed on the horizontal axis, and the vertical axis shows the survival rate of mice in percents.
Figure 2:
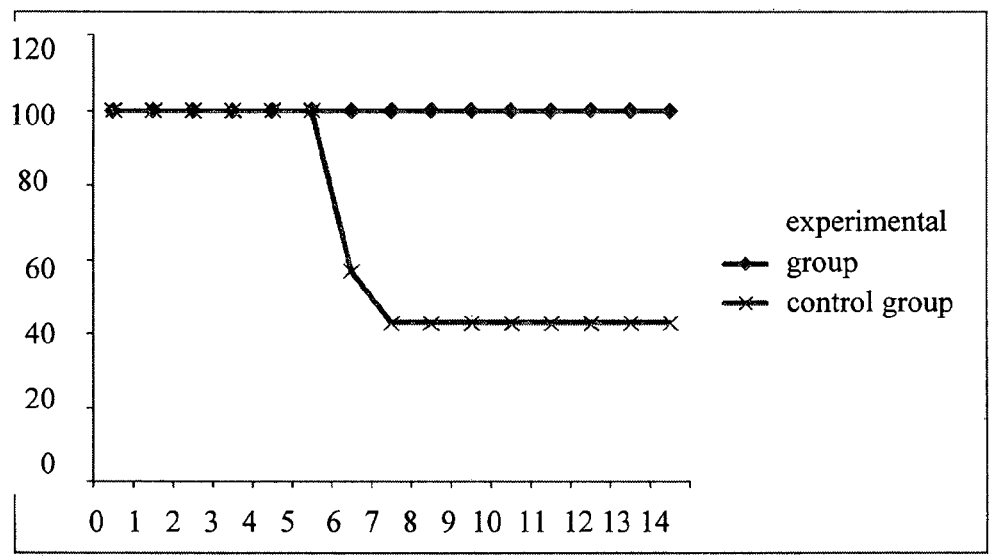
FIG. 2. Dynamics of mice survival rate after infection with 1 LD/50 of virus A/California/07/09(H1N1). The days post infection are displayed on the horizontal axis, the survival rate of mice in percents—on the vertical axis.

After all the steps mentioned above, the construction resulted that is shown in FIGS. 1, 2.

The modeled fusion protein consists of 593 amino acid residues; its amino acid sequence is given —SEQ ID NO:1. Analysis of the amino acid sequence of this protein via ProtParam program (expasy.org/tools/protparam) has shown that the molecular weight of the fusion protein is 63.6 kDa, pl 6.2.

EXAMPLE 2

Production of Nucleotide Sequence Encoding the Fusion Protein

The amino acid sequence of the fusion protein that included FliC1, FliC2, H1, H3, H5, B fragments was translated into the nucleotide sequence (1785 bp), which was then optimized for the expression in *E. coli* cells (SEQ ID NO:2).

The synthesis of the present nucleotide sequence was performed via elongation of the overlapping oligonucleotides according to the described methods (Majumder, 1992). The oligonucleotides represented fragments of the fusion gene being 70 nucleotides long, containing overlapping regions of 20 nucleotides. The main primer requirements were as follows: their length should not exceed 60 nucleotides, while the fusionization sites should not be shorter than 20 nucleotides. Furthermore, there should not be long terminal G/C repeats. In certain cases, selection of the optimal primers was performed empirically via primer-template movement or primer length changing by 3-6 nucleotides. Altogether, for synthesis of the 1785 bp long fusion gene, 65 primers were used. The synthesized fragments (300 bp each) were extracted via gel-electrophoresis and cloned into the plasmid vector pGEM-T Easy. The cloning was performed using restriction sites KpnI, SacII, EcoRV, BamHI or via blunt ends, as the case may be. After sequencing, the fragments were amplified and then joined into a nucleotide sequence of the fusion protein via polymerase chain reaction (PCR). After the final stage of the fusion gene synthesis via DNA fragment ligation, the artificial gene was cloned into the pGEM-T vector via KpnI and SacI restriction sites. The produced gene was flanked by additional restriction sites: EcoRI at the 5' end and XhoI at the 3' end. Next, the artificial gene was recloned into the expression vector pET24a via EcoRI and XhoI restriction sites.

EXAMPLE 3

Production of Plasmid DNA Encoding the Fusion Protein

According to the methods described in the example 2, a nucleotide sequence was obtained for the purpose of production of the influenza vaccine.

The resulting gene was cloned into the pET24a plasmid for the purpose of subsequent expression in *E. coli* cells. Therefore, ligation of the gene and the pET24a vector via appropriate buffer and ligase was performed. The reaction was being performed at +20° C. for 2 hours.

The mixture was being warmed up at +95° C. for 10 min. Afterwards, saults were removed via dialysis through nitrocellulose membrane filters with the pore size of 0.025 μm (Millipore, USA). The dialysis was being performed against solution containing 0.5 mM EDTA in 10% glycerol for 10 min.

EXAMPLE 4

Production of the *E. coli* Strain for Amplification of the Plasmid DNA Containing the Fusion Gene According to the methods described in the example 3, a nucleotide sequence of the gene was produced for the purpose of creation of the influenza vaccine, and then it was cloned into the pET24a vector. The *E. coli* cells of the strain DH10B/R (Gibko BRL, USA) possessing following genotype: F-mcrA Δ(mrr-hsdRMS-mcrBC) ϕ80dlacZzΔM 15 ΔlacX74 deoR recA1 endA1 araD139 Δ(ara, leu)769 galKλ-rpsL nupG were transformed with the resulted plasmid via electroporation.

After transformation, the cells were being incubated in SOC medium (2% bacto-tryptone, 0.5% yeast extract, 10 mM NaCl, 2.5 mM KCl, 10 mM MgCl2, 10 mM MgSO4, 20 mM glucose) for 40 min at +37° C.

After screening of the *E. coli* cells for possessing the plasmid—in the selective medium containing LB-agar and 100 μg/ml kanamycin,—the appropriate colonies of *E. coli* cells were sampled to obtain the *E. coli* strain for the subsequent amplification of the plasmid DNA containing the fusion gene.

The plasmid DNA was extracted from the grown clones via Wizard Minipreps DNA Purification System kit (Promega, USA).

The purified plasmid DNA was analyzed via restriction assay and sequencing. In course of research, the clones were sampled, which contained DNA fragments of required size in their plasmids. Next, such plasmids were extracted for the subsequent induction of the gene expression.

EXAMPLE 5

Obtaining the *E. coli* Strain Producing the Fusion Protein

According to the methods described in the example 4, the nucleotide sequence of the protein was obtained for the purpose of production of the influenza vaccine and then was cloned into the pET24a plasmid; the resulted plasmid was amplified in the *E. coli* cells of the strain DH10B/R and then extracted.

For the expression of the protein, the *E. coli* cells of the strain BL21 Star (DE3) (Invitrogen, USA) with following genotype: F-ompT hsdSB (rB-mB) gal dcm rne131 (DE3) containing λDe3 lysogen and rne131 mutation in genome were used. The mutant rne-gene (rne131) encodes a short version of RNase E, so that intracellular mRNA degradation is reduced and its fermentative stability is increased. The Ion- and ompT-mutations in protease genes allow obtaining high yields of non-proteolyzed recombinant proteins.

The *E. coli* cells of the strain BL21 with the genotype F-ompT hsdSB (rB-mB) gal dcm rne131 (DE3) were prepared as following. The cells were being incubated at +37° C. overnight in 5 ml L-broth, containing 1% tryptone, 1% yeast extract and 1% sodium chloride. The culture was diluted 50-100 fold in fresh L-broth and was being cultivated in a shaking incubator at +37° C. until the optical density of 0.2-0.3 at 590 nm was measured. After having reached 0.3 OD, the culture was diluted in the fresh L-broth until 0.1 OD and was being cultivated for 30 min. The culture in the volume of 100 ml was transferred to a sterile centrifuge tube, and cell pelleting was being performed at +4° C., 5000 g for 10 min. The supernatant was discarded, and the cells were resuspended in deionized water to the initial volume under subsequent centrifuging. The washing steps were repeated three times. After washing, the cell pellet was resuspended in a small volume of deionized water and the suspension was being centrifuged for 30 sec at 5000 rpm in a microcentrifuge.

The transformation of the competent cells was performed via electroporation. Therefore, 1 µl of plasmid DNA was added to 12 µl of competent cells, and the suspension was mixed. The subsequent electroporation was performed via pulse generator GVI-1 (St. Petersburg State Polytechnical University, St. Petersburg) in sterile chambers at 10 kV/cm for 4 msec.

After transformation, the cells were being incubated in SOC medium (2% bacto tryptone, 0.5% yeast extract, 10 mM NaCl, 2.5 mM KCl, 10 mM MgCl2, 10 mM MgSO4, 20 mM glucose) for 40 mM at +37° C. 10-100 µl cell suspension was transferred to selective LB medium (Gibco BRL, USA) containing kanamycin (100 µg/ml) for selection of the clones with the plasmids (producer strains).

The plasmid obtained after transformation of the competent $E.$ $coli$ cells provided a high level of expression of the encoded recombinant protein.

EXAMPLE 6

Production of the Fusion Protein for the Creation of the Influenza Vaccine in $E.$ $coli$ Cells Via Induction of Protein Synthesis by 0.2% Lactose According to Studier Method According to the methods described in the example 5, the nucleotide sequence of the fusion protein for the creation of the influenza vaccine was obtained and cloned in the pET24a plasmid; the obtained plasmid was amplified in $E.$ $coli$ cells of the strain DH10B/R, extracted, and $E.$ $coli$ cells of the strain BL21 were transformed thereby for the purpose of induction of the target gene expression.

For the purpose of cultivation of the obtained producer strains, standard agarized LB medium containing kanamycin (100 µg/ml) and 1% glucose for blocking of nonspecific expression was used.

The expression was induced after the cell culture had reached the optical density of 0.6-0.8 at 600 nm. 0.2% lactose was used as inductor (Studier, 2005).

For autoinduction of the expression according to the Studier's method (Studier, 2005), PYP-5052 medium was used, containing 1% peptone (Gibco, USA), 0.5% yeast extract (Gibco, USA), 50 mM $Na_2HPO_4$, 50 mM $K_2HPO_4$, 25 mM $(NH_4)_2SO_4$, 2 mM $MgSO_4$, 0.5% glycerol, 0.05% glucose and 0.2% lactose.

A single producer strain colony was inoculated into PYP-5052 medium, containing kanamycin (100 µg/ml). The fermentation was being performed at +37° C. in a thermostatic shaker at 250 rpm for 20 hours until no significant change in the $OD_{600}$ per hour measured. An aliquot of the cells was taken for the purpose of expressional analysis of the gene encoding the vaccine protein. The expressional analysis was performed via polyacrylamide gel electrophoresis (PAGE). The rest of the biomass was pelleted in the centrifuge at 9000 g.

The protein was extracted from the $E.$ $coli$ cells via cell lysis. The cells were resuspended in the lysis buffer, containing 20 mM tris-HCl pH 7.5, 5 mM EDTA, and 1 mM phenoxymethylsulfonylfluoride (PMSF), on 1 g cells per 5-7 ml buffer basis. The cell suspension was exposed to ultrasound 7 times for 30 sec at a 30 sec interval (22 kHz). The lysate was being centrifuged for 10 min at +4° C., 5000 g. The supernatant was discarded, and the pellet was resuspended in 1 M urea solution on 10 ml per 1 g cells basis by intensive mixing. The centrifuge step was repeated. The supernatant was discarded, and the pellet was resuspended in 2 M urea solution of the same volume. The centrifuge step was repeated. The supernatant was discarded.

According to the SDS-Page (Polyacrylamide Gel Electrophoresis with Sodium Dodecyl Sulfate) data the obtained product contained approximately 98% of the fusion protein at concentration of 1 mg/ml.

The extraction and purification conditions were adjusted experimentally and can vary to some extent that a person of ordinary skill in the art familiar with.

EXAMPLE 7

Obtention of Preparation of Purified Fusion Protein $MgCl_2$ was added to the fusion protein solution to reach the concentration of 6 mM. The fusion protein was purified via Immobilized-Metal Affinity Chromatography (IMAC) using Ni-NTA Sepharose. The capture by this sorbent is performed due to 6 histidine residues on the N-terminus of the obtained recombinant protein. The protein solution filtering was performed via PVDF filter with a pore diameter of 0.22 µm. To the so obtained filtrate the sorbing agent— Ni-NTA sepharose—was given, which was equilibrated with refolding buffer, making allowance of the fact that 1 ml of the sorbent can bind not more than 40 mg of protein. The capture was being performed for 2 hours. The sorbent was pelleted via centrifugation and transferred to a gravity chromatography column, containing 2 ml of the sorbent.

The step gradient elution was performed with 20-300 mM imidazole by 50% of the previous concentration at each step, using eluting solution at a volume of 5-20 fold of the column volume. The yield and purity of the protein was controlled via disc electrophoresis and Bradford protein assay.

For determination of the endotoxin content, standard stock endotoxin solution with the defined potency of 4000 EU was prepared. The produced solution was stable for at least two weeks, when preserved at +4° C. A two-fold serial dilution was prepared in sterile polystyrene tubes, using endotoxin-free water. The tubes were sealed with endotoxin-free parafilm. A five-fold and—after the preparatory endotoxin content evaluation—a two-fold serial dilution of the sample were prepared. The sample, water, 100 µl of endotoxin, and, at last, 100 µl of LAL-reactive were put on the bottom of each eppendorf tube. The mixture was being incubated for 1 hour at 37° C. in a water bath. The results were estimated by means of presence or absence of a firm clot on the bottom of the inverted tube.

The absence of factors that inhibit clot formation in the analyzed sample was shown. The gel clot was formed at a ⅛ sample dilution, it means that, taking into consideration the method sensitivity of 0.03 EU/ml, the sample with the concentration of 50 µg/ml contained less than 100 EU.

The conformation of the recombinant fusion protein during its biosynthesis in $E.$ $coli$ was determined via polyacrylamide discontinuous electrophoresis of the disrupted by sonication $E.$ $coli$ cells, after the induction of the expression. In addition, both pellet and supernatant, formed after sedimentation of the cell lysate, were analyzed. Densitometric analysis demonstrated that 100% of the recombinant protein, synthesized in E. coli producer strain, was accumulated in the supernatant, i.e. in the soluble fraction.

Cultivation of bacteria at different temperatures: 20° C., 30° C. and 37° C., did not affect protein solubility.

After autoinduction of the expression in E. coli with 0.2% lactose and subsequent polyacrylamide disc electrophoresis of the cell lysates, the densitometric analysis of target protein expression in E. coli was performed. The densitometric analysis demonstrated that the fusion protein accumulates and amounts 43% of total cellular protein content.

The obtained expression level did not change in the producer strain for 6 passages, which indicates a stable expression of the analyzed gene.

EXAMPLE 8

Production of the Recombinant Fusion Protein Via Cultivation of E. coli Cells with Continuous Nutrient Supply (Preferred Nutrients: Glucose and Yeast Extract)

A fed-batch culture of Escherichia coli strain was used for the purpose of production of the fusion protein. This method is preferred, when it is necessary to avoid substrate limitation and its negative consequences. Thereby, a substrate or any other essential components are being supplied either continuously, or in response to sensor signals. For the purpose of optimization of the yields of product being secreted in the medium, it is important to increase the biosynthetic capabilities of the bacterial cells, while the cultivation mode will extend the second growth phase and increase the yields of extracellular metabolites. This method can be used in case of a potentially toxic substrate (recombinant proteins are toxic for the E. coli cells), as its concentration in the medium will be kept at a low level.

Due to overcome of catabolite repression of the product synthesis, the speed of substrate uptake can be limited by the speed of its transport.

Fed-batch culture appeared to be the most effective way to achieve a high cell density and high productivity.

The E. coli strain was passaged on the angular EDTA-containing agar under sterile conditions and was being incubated in the thermostat for 5 days. To obtain the inoculate, the culture was washed from the agar, passaged to a liquid EDTA-containing medium with, and cultivated for 3-4 days. Next, 10 ml inoculate was passaged into 750-ml flasks, containing 200 ml of sterile liquid medium, and cultivated in a thermostatic shaker at 150-200 rpm, 28° C.-30° C. for 10 days.

Gel growth medium was used to obtain fresh culture of the strain.

The liquid growth medium was used to obtain the seed material and for periodic cultivation.

Preparation of the Liquid Growth Medium
1) $MgSO_4*7 H_2O$ 10 ml/l
2) $CaCl_2*2 H_2O$ 20 ml/l
3) $KH_2PO_4+NaH_2PO_4*12 H_2O$ 10 ml/l
4) EDTA 10 ml/l
5) Microelements 1 ml/l
(pH adjusted to 4.2)+5.6 g/l EDTA:
$FeCl_2*4 H_2O$ 1.5 g/l
$H_3BO_3$ 0.06 g/l
$MnCl_2*6 H_2O$ 0.1 g/l
$CaCl_2*6 H_2O$ 0.12 g/l
$ZnCl_2$ 0.07 g/l
$NiCl_2*6 H_2O$ 0.025 g/l
$CuCl_2*2 H_2O$ 0.015 g/l
$Na_2MoCl_4$ 0.025 g/l
6) Vitamins
Pyridoxine 20 mg
Thiamine 10 mg
Riboflavin 10 mg
Nicotinic acid 10 mg
4-Aminobenzoic acid 10 mg
Alpha lipoic acid 10 mg
Nicotinamide 10 mg
Vitamin B12 10 mg
Biotin 4 mg
Folic acid 4 mg All components were dissolved in 200 ml of water, sterilized at 0.5 atm for 30 min, and added to a liquid nutrient broth medium at the rate of 1 ml/l.

The compounds of the growth medium were weighted on technical and analytical balances and dissolved in distilled water. According to the previous experience, we prepared growth media out of presterilized concentrated solutions.

The gel growth medium was produced both as a liquid and with 3% agar.

The optical density ($OD_{600}$) of the E. coli cell culture was 9. The cells were sedimented via centrifugation at 13000 g for 6 min at 10° C. The cell pellet was weighted; its weight was 2.1 g.

The cells were resuspended in 30 ml buffer (50 mM TrisHCl, 50 mM EDTA, 20 mM L-cysteine, pH 8.6) and disrupted by ultrasound (sonication time—10 min, impulse time—30 sec, pause between the impulses—30 sec, amplitude—70%). After the cell breakage, the inclusion bodies were pelleted under centrifugation at 30000 g for 20 min at 10° C.; the wet weight of the inclusion bodies was 1.45 g. the pelleted inclusion bodies were washed with several buffers according to the following scheme:
1. The pellet containing inclusion bodies was resuspended in 10 ml (the last wash—15 ml) of washing buffer
2. The resuspended inclusion bodies were mixed on a horizontal shaker for 1 hour at a room temperature
3. The inclusion bodies were pelleted via centrifugation at 30000 g for 20 min at 10° C.

After five washing steps, the wet weight of the inclusion bodies was 0.7 g.

For the purpose of protein solubilization out of the inclusion bodies, 18 ml of solution (9 M urea, 2 mM EDTA, 50 mM TrisHCl, pH 8.6) was used. The solubilized inclusion bodies were being centrifuged at 30000 g for 20 min at 10° C. The developed supernatant was transferred in to the new falcons and was used for the refolding.

The refolding step was performed as follows: the solubilized inclusion bodies were 10-fold diluted in the refolding buffer at +4° C. dropwise. $MgCl_2$ was added to the refolded protein until 6 mM. Protein purification was performed via Immobilized-Metal Affinity Chromatography (IMAC) using Ni-NTA Sepharose. The protein solution was filtered via PVDF filter with a pore diameter of 0.22 μm. To the so obtained filtrate the sorbing agent—Ni-NTA sepharose—was given, which was equilibrated with refolding buffer, taking into consideration the fact that 1 ml of sorbent can bind not more than 40 mg of protein. The capture was being performed for 2 hours. The sorbent was pelleted via centrifugation and was given at a minimal volume onto a gravity chromatography column containing 2 ml of sorbent.

The step gradient elution was performed with 20-300 mM imidazole (20, 40, 100, 150, 200 и 300 mM), whereas at each step the volume of the eluting solution was 10 fold of the column volume.

In this way, 41 mg of fusion protein with the purity of 97% was obtained.

EXAMPLE 9

Production of the Fusion Protein, being Purified Before Dilution, and Removal of Soluble Cell Components Including DNA, RNA, Proteins, Lipopolysaccharides Via Washing with Buffer Solution, Containing a Guanidine Hydrochloride Detergent Upon fermentation, cell breakage, and washing of the inclusion bodies (see Example 8), protein was solubilized in 18 ml of solution (8 M GuHCl, 2 mM EDTA, 50 mM TrisHCl, pH 8.6), containing guanidinium chloride. The solubilized inclusion bodies were pelleted under centrifugation at 30000 g for 20 min at 10° C. The obtained supernatant was transferred to new falcons and used for refolding.

Next, refolding and purification of the recombinant protein were performed (see Example 8). As a result of purification, 41 mg of the fusion protein was obtained, with a purity rate of 98%.

EXAMPLE 10

Determination of Immunogenicity of the Obtained Protein

An immunogenicity test of the obtained protein was performed. Immunogenicity is a capability of an antigen to initiate production of effectors that neutralize antigenic foreignness by immune system. In order to induce immune response, an antigen should be immunogenic. The point to be emphasized is that immunogenicity is a complex feature, which depends on the properties of the antigen itself, the way of its penetration, and the way of immunization.

Mice were immunized abdominally with 20 µg of the fusion protein. The immunization was performed twice, spaced two weeks apart. The animals were divided into experimental and control groups with 5-6 mice in each group.

Blood samples were taken from the tail vein from 5-6 mice out of each group two weeks after the second immunization. To obtain serum, blood was incubated for 30 minutes at 37° C. After clot formation, the samples were transferred on ice, cooled down for 1 hour, and then centrifuged for 15 minutes at 400 g. Mice blood sera from each group were pooled and frozen at −20° C.

Antibody titers in the sera of the immunized mice were determined via enzyme-linked immunosorbent assay, (ELISA). ELISA was performed according to conventional technology. 96-well plates were used (Greiner, Germany), on which the fusion protein was sorbed (in carbonate buffer, pH 9.5-9.6) and incubated over night at 4° C.

The fusion protein was denaturated as follows. To the protein sample a detergent Tween-20 was being added, until the end-concentration of 1% (w/v) was reached. Next, the sample was being incubated in a water bath for 1 hour at 37° C. After the incubation step, the sample was being centrifuged for 1 hour at 200° C. and 2000 g, and supernatant, containing the fusion protein, was taken. The detergent was liquidated via Detergent-OUTtmMicro Kit (Millipore); the detergent-free sample was being concentrated on the Speed-Vac until the original volume. Additional treatment of the product was performed with 8M urea and dithiothreitol (0.02M) upon subsequent dialysis over night against carbonate buffer (pH=8.5).

The microtiter plates were being treated by blocking buffer (0.01 M PBS, pH=7.2-7.4 with 5% FCS) for 1 hour at room temperature and then washed three times with PBS containing Tween-20. 100 µl two-fold serum dilutions in blocking buffer (beginning with 1:200) were given to plate wells and incubated for 1 hour at room temperature. The serum was analyzed in duplicate. As a conjugate, polyclonal rabbit anti-mouse radish peroxidase-conjugated IgG antibodies (Abcam, UK), diluted 1:8000, were used. TMB was used as a substrate. Detection was performed at 450 nm. The endpoint titer was the highest dilution that gives an optical density of 2 standard deviations above negative control—serum of non-immunized mice at the same dilution.

The results show a high immunogenicity of the obtained protein. After immunization with the fusion protein, antibodies to the antigen were detected, titer is 51200.

Therefore, development of a strong immune response in mice immunized with the fusion protein was demonstrated.

EXAMPLE 11

Protective Effect of the Vaccine Based on the Fusion Protein Against Different Influenza Virus Strains In the present research 30 Balb/c female mice aged 7-8 weeks (16-18 g weight) were used, which were received from the branch of the Shemyakin-Ovchinnikov Institute of Bioorganic Chemistry, RAS (IBCh RAS)—Animals Breeding Center "Pushchino". The laboratory animals were healthy and helminths-free (veterinary certificate 250 No 0187942 of Nov. 27, 2012). The animals were kept in the animal facility of the Ministry of Healthcare of the Russian Federation Research Institute of Influenza according to the existing sanitary regulations.

Mice were immunized abdominally with 20 µg of the recombinant fusion protein. The immunization was performed twice, with two weeks interval.

To analyze protectivity of the fusion protein on the model of lethal influenza infection, the mouse-adapted influenza virus strains A/California/07/2009 (H1N1) and A/PR/8/34 (H1N1) were used. Virus titration for determination of a dose causing death of 50% of animals was performed on Balb/c mouse line (female mice, aged 6-7 weeks). Frozen virus was thawed, the mice lethal dose (causing 50% fatality) was estimated via introduction with ten-fold virus dilution (4 mice pro dilution). Mice were monitored for 14 days post introduction. Virus titer was estimated using Reed and Muench mathematical technique. Mice were inoculated intranasally with the dosages of 1 LD/50 (dose causing 50% mortality in mice) and 5 LD/50 (dose causing 90% mortality in mice) at the rate of 50 µl/mice under slight ether narcosis. After introduction, the animals were monitored for 14 days.

Mice began to die on the sixth day after introduction. The survival rate in the control group was 43%. In the experimental group 100% survival rate was observed (FIG. 1).

Mice began to die on the sixth day after introduction. The survival rate in the control group estimated 42%. In the experimental group 100% survival rate was observed (FIG. 2).

EXAMPLE 12

Development of Polyvalent Immune Response to Different Influenza A and B Virus Strains Via Mouse Immunization with the Fusion Protein In the present research Balb/c female mice aged 7-8 weeks (16-18 g weight) were used, which were received from the branch of the Shemyakin-Ovchinnikov Institute of Bioorganic Chemistry, RAS (IBCh RAS)—Animals Breeding Center "Pushchino". The laboratory animals were healthy and helminths-free (veterinary certificate 250 No 0187942 of Nov. 27, 2012). The animals were kept in the animal facility of the Ministry of Healthcare of the Russian Federation Research Institute of Influenza according to the existing sanitary regulations.

Mice were immunized abdominally with 20 µg/200 µl of the fusion protein. The immunization was performed twice, with two weeks interval. The animals were divided into experimental and control groups with 5-6 mice in each group.

Blood samples were taken from the tail vein from 5-6 mice out of each group two weeks after the second immunization. To obtain serum, blood was being incubated for 30 minutes at 37° C. After clot formation, the samples were transferred on ice and cooled down for 1 hour, then centrifuged for 15 minutes at 400 g. Mice blood sera from each group were pooled and frozen at −20° C.

Antibody titers in the sera of the immunized mice were determined via enzyme-linked immunosorbent assay, (ELISA). ELISA was performed according to conventional technology. 96-well plates were used (Greiner, Germany), on which antigens from the strains A/California/07/09 (H1N1), A/PR/8/34 (H1N1), A/Perth/16/09 (H3N2), A/Chicken/Kurgan/05/2005 (H5N1) were sorbed at a concentration of 2 µg/ml (in carbonate buffer, pH 9.5-9.6) and incubated over night at 4° C.

The fusion protein was denaturated as follows. Detergent Tween-20 was being added to the protein sample until the end-concentration of 1% (w/v) was reached. Next, the sample was being incubated in a water bath for 1 hour at 37° C. After the incubation step, the sample was being centrifuged for 1 hour at 200° C. and 2000 g, and supernatant containing the fusion protein was taken. The detergent was liquidated via Detergent-OUTtmMicro Kit (Millipore); the detergent-free sample was being concentrated on the Speed-Vac until the original volume. Additional treatment of the product was performed with 8M urea and dithiothreitol (0.02M) upon subsequent dialysis over night against carbonate buffer (pH=8.5).

The microtiter plates were being treated by blocking buffer (0.01M PBS, pH=7.2-7.4 with 5% FCS) for 1 hour at room temperature and then washed three times with PBS containing Tween-20. 100 µl two-fold serum dilutions in blocking buffer (beginning with 1:200) were given to plate wells and incubated for 1 hour at room temperature. All sera were analyzed in duplicate. Polyclonal rabbit anti-mouse radish peroxidase-conjugated IgG antibodies (Abcam, UK), diluted 1:8000, were used as a conjugate. TMB was used as a substrate. Detection was performed at 450 nm. The end-point titer was the highest dilution that gives an optical density of 2 standard deviations above negative control—serum of non-immunized mice at the same dilution.

TABLE 1

Titers of serum antibodies (IgG) after dualfold immunization of mice with fusion protein.

| | Sorbed antigens (virus) | | | | |
|---|---|---|---|---|---|
| | A/California/ 07/09 (H1N1) | A/PR/ 8/34 (H1N1) | A/Perth/ 16/09 (H3N2) | A/Kurgan/ 05/2005 Tw (H5N1) | B/Florida/ 04/06 |
| IgG titers in blood sera of Balb/c mice, Fusion protein | 51 200 | 12 800 | 3 200 | 6 400 | 6 400 |

In course of immunization with the fusion protein, antibodies against all examined strains of influenza A virus at the rates of 1:3200 in the case of H3N2 A/Perth/16/09 up to 1:51200 in the case of H1N1 A/California/07/09 were found in murine blood.

Thus, development of polyvalent immune response against different strains of influenza A and B virus in mice immunized with the fusion protein was demonstrated.

EXAMPLE 13

Capability of the Antibodies Formed after Immunization of Animals with Inactivated Influenza B Virus to Bind to the Fusion Protein In the Present Research, Rabbits from the Genus Chinchilla of 2-2.5 kg Weight were used. The rabbits were taken from the laboratory animal bank of Russian Academy of Medical Sciences, village Rappolovo, Leningrad oblast. The animals were kept in the animal facility of the Research Institute of Influenza, North-West Branch of the Russian Academy of Medical Sciences according to the existing sanitary regulations.

The capability of the antibodies formed after immunization of animals with inactivated influenza B virus to bind to the fusion protein was studied on rabbits. The animals were immunized twice, with one month interval, subcutaneously with inactivated influenza virus B/Florida/04/with Freund's adjuvant at the dosage of $10^9$ PFU. Blood was taken from the ear vein 1.5 months after the second immunization. Titers of serum antibodies (IgG) against influenza virus B/Florida/04/06 and the fusion protein were estimated via ELISA (Anti Rabbit Ig-HRP conjugate, Sigma-Aldrich, A 6154, diluted 1:5000). Blood serum from non-immunized rabbits was used as a negative control. The results of the performed research show that antibodies against the surface proteins of influenza virus strain B/Florida/04/06 are capable of binding fusion protein; titers of antibodies against the fusion protein were 1:204000.

Figure 3:
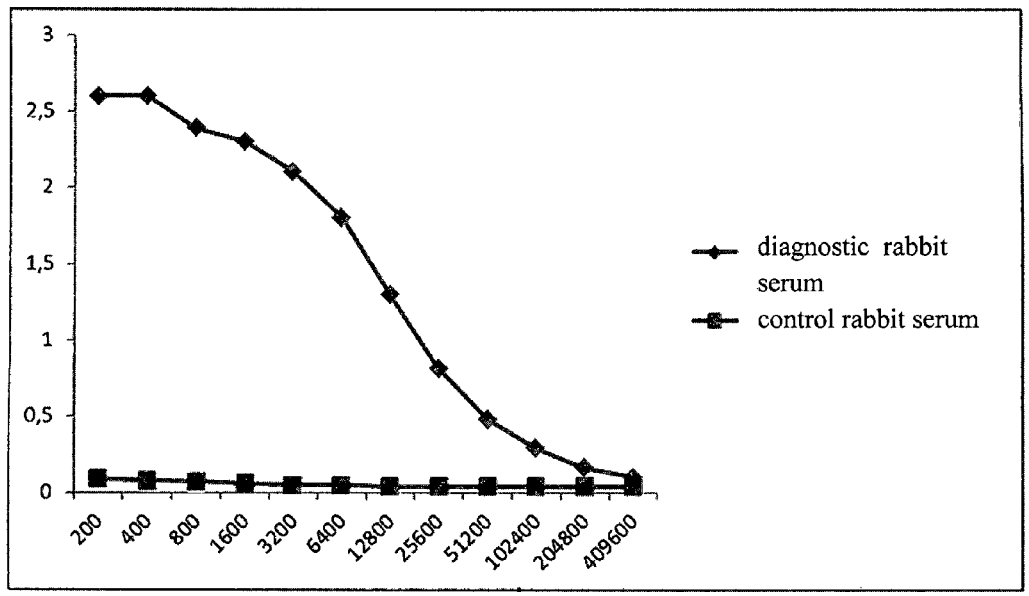
FIG. 3. Serum IgG against influenza B/Florida/04/06 virus. Serum IgG against the fusion protein. Serum dilution (the reciprocal value) is displayed on the horizontal axis, and the optical density at 450 nm—on the vertical axis.
Figure 4:
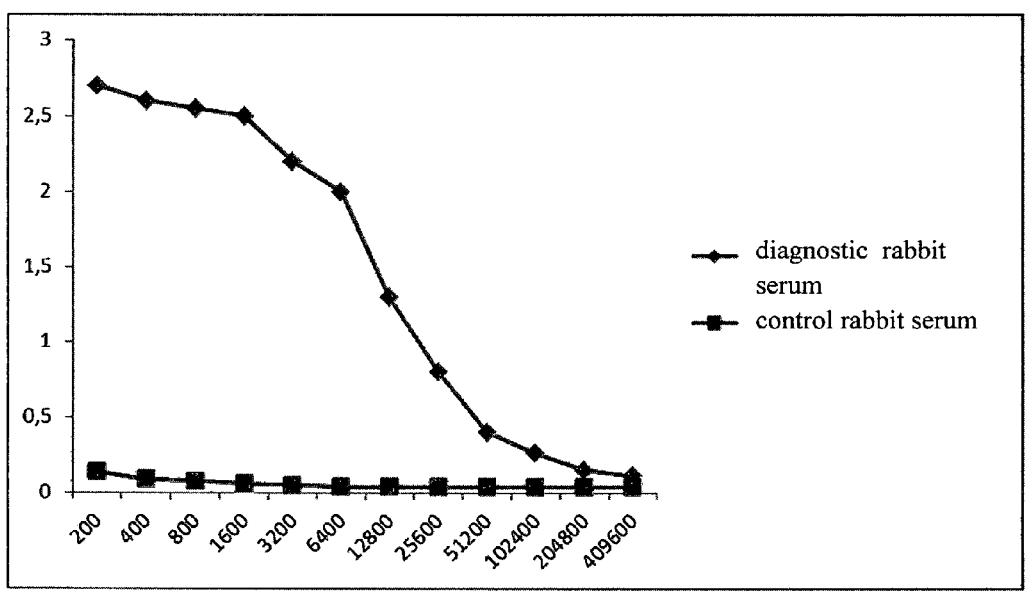
FIG. 4. Serum IgG against the fusion protein. Serum dilution (the reciprocal value) is displayed on the horizontal axis, and the optical density at 450 nm—on the vertical axis. The recombinant protein was entrapped at the concentration of 3 µg/ml.

Titers of serum antibodies (IgG) against influenza virus strain B/Florida/04/06 and the fusion protein were estimated via ELISA (Anti Rabbit Ig-HRP conjugate, Sigma-Aldrich, A 6154, diluted 1:5000). The results are shown on the FIG. 3 and FIG. 4. The titers of antibodies in ELISA against influenza virus strain B/Florida/04/06 and the fusion protein were 409,600 and 204,800, correspondingly.

Thus, immunologic polyvalence of the fusion protein against influenza A and B viruses has been demonstrated.

The invention claimed is:

1. A polyvalent influenza A and B virus vaccine comprising a fusion protein that comprises SEQ ID NO: 1, wherein the vaccine is capable of producing immune responses which reduce infections by influenza A and B viruses.

2. The polyvalent, influenza vaccine of claim 1, wherein the fusion protein is encoded in a nucleotide sequence that comprises SEQ ID NO: 2.

3. The polyvalent influenza vaccine of claim 1, wherein the vaccine is produced as a result of:
creation of a recombinant DNA encoding the fusion protein,
insertion of this DNA in a vector construct for expression in cells of *Escherichia coli*,
transfer of this vector construct into cells of *Escherichia coli*,
production of the fusion protein in *Escherichia coli* cells, and
extraction and purification of the fusion protein and mixing with a physiologically acceptable excipient.

4. The polyvalent influenza vaccine of claim 2, wherein the vaccine is produced as a result of:
creation of a recombinant DNA encoding the fusion protein,
insertion of this DNA in a vector construct for expression in cells of *Escherichia coli*,
transfer of this vector construct into bacterial cells of *Escherichia coli*, production of the fusion protein in *Escherichia coli* cells, and extraction and purification of the fusion protein and mixing with a physiologically acceptable excipient.

* * * * *

SEQUENCE LISTING

<160> NUMBER OF SEQ ID NOS: 2

<210> SEQ ID NO 1
<211> LENGTH: 593
<212> TYPE: PRT
<213> ORGANISM: Artificial Sequence
<220> FEATURE:
<221> NAME/KEY: DOMAIN
<222> LOCATION: (1)...(169)
<223> OTHER INFORMATION: FliC domain 1, from 1 to 169 amino acids of
    gb`B33952.1[0ac]Tr;;63<220> FEATURE:
<221> NAME/KEY: DOMAIN
<222> LOCATION: (182)...(276)
<223> OTHER INFORMATION: FliC domain 2, from 311 to 405 amino acids of
    gb`B33952.1[0ac]Tr;;63<220> FEATURE:
<221> NAME/KEY: DOMAIN
<222> LOCATION: (281)...(461)
<223> OTHER INFORMATION: H1 epitope, of ifluenza A virus haemagglutinin
<220> FEATURE:
<221> NAME/KEY: DOMAIN
<222> LOCATION: (466)...(505)
<223> OTHER INFORMATION: H3 epitope, of ifluenza A virus haemagglutinin
<220> FEATURE:
<221> NAME/KEY: DOMAIN
<222> LOCATION: (510)...(549)
<223> OTHER INFORMATION: H5 epitope, of ifluenza A virus haemagglutinin
<220> FEATURE:
<221> NAME/KEY: DOMAIN
<222> LOCATION: (554)...(593)
<223> OTHER INFORMATION: epitope of ifluenza B virus haemagglutinin

<400> SEQUENCE: 1

Ala Gln Val Ile Asn Thr Asn Ser Leu Ser Leu Leu Thr Gln Asn Asn
 1               5                  10                  15

Leu Asn Lys Ser Gln Ser Ala Leu Gly Thr Ala Ile Glu Arg Leu Ser
            20                  25                  30

Ser Gly Leu Arg Ile Asn Ser Ala Lys Asp Asp Ala Ala Gly Gln Ala
        35                  40                  45

Ile Ala Asn Arg Phe Thr Ala Asn Ile Lys Gly Leu Thr Gln Ala Ser
    50                  55                  60

Arg Asn Ala Asn Asp Gly Ile Ser Ile Ala Gln Thr Thr Glu Gly Ala
65                  70                  75                  80

Leu Asn Glu Ile Asn Asn Asn Leu Gln Arg Val Arg Glu Leu Ala Val
                85                  90                  95

Gln Ser Ala Asn Ser Thr Asn Ser Gln Ser Asp Leu Asp Ser Ile Gln
            100                 105                 110

Ala Glu Ile Thr Gln Arg Leu Asn Glu Ile Asp Arg Val Ser Gly Gln
        115                 120                 125

Thr Gln Phe Asn Gly Val Lys Val Leu Ala Gln Asp Asn Thr Leu Thr
    130                 135                 140

Ile Gln Val Gly Ala Asn Asp Gly Glu Thr Ile Asp Ile Asp Leu Lys
145                 150                 155                 160

Gln Ile Asn Ser Gln Thr Leu Gly Leu Gly Gly Ser Gly Gly Gly
                165                 170                 175

Ser Gly Gly Gly Ser Ala Ala Thr Thr Thr Glu Asn Pro Leu Gln Lys
            180                 185                 190

Ile Asp Ala Ala Leu Ala Gln Val Asp Thr Leu Arg Ser Asp Leu Gly
        195                 200                 205

Ala Val Gln Asn Arg Phe Asn Ser Ala Ile Thr Asn Leu Gly Asn Thr
    210                 215                 220

Val Asn Asn Leu Thr Ser Ala Arg Ser Arg Ile Glu Asp Ser Asp Tyr
225                 230                 235                 240

Ala Thr Glu Val Ser Asn Met Ser Arg Ala Gln Ile Leu Gln Gln Ala
            245                 250                 255

Gly Thr Ser Val Leu Ala Gln Ala Asn Gln Val Pro Gln Asn Val Leu
        260                 265                 270

Ser Leu Leu Arg Gly Gly Ser Ile Ala Ile Arg Pro Lys Val Arg
    275                 280                 285

Asp Gln Glu Gly Arg Met Asn Tyr Tyr Trp Thr Leu Val Glu Pro Gly
290                 295                 300

Asp Lys Ile Thr Phe Glu Ala Thr Gly Asn Leu Val Val Pro Arg Tyr
305                 310                 315                 320

Ala Phe Ala Met Glu Arg Asn Ala Gly Ser Gly Ile Ile Ile Ser Asp
                325                 330                 335

Thr Pro Pro Tyr Asn Asp Lys Phe Asp Lys Leu Tyr Ile Trp Gly Val
            340                 345                 350

His His Pro Ser Thr Asp Ser Asp Gln Thr Ser Leu His His Arg Leu
        355                 360                 365

Ile Glu Lys Thr Asn Glu Lys Phe His Gln Ile Glu Lys Glu Phe Ser
    370                 375                 380

Glu Val Glu His His Tyr Asp His Asp Val Tyr Arg Asp Glu Ala Leu
385                 390                 395                 400

Asn Asn Arg Phe Gln Ile Lys Gly Val Glu Leu Lys Ser Gly Tyr Thr
                405                 410                 415

Ile Gly Thr Thr Ile Ala Thr Ser Arg Gly Val Gly Thr Leu Gln Thr
            420                 425                 430

Lys Asn Thr Ile Thr Phe Met Thr Gln Met Ser Arg Thr Phe Thr Thr
        435                 440                 445

Arg Ser Asp Tyr Ser Leu Gly Ile Met Gln Arg Ser Leu Gly Gly Gly
450                 455                 460

Ser Arg Ser Lys Ala Phe Ser Asn Cys Tyr Pro Tyr Asp Val Pro Asp
465                 470                 475                 480

Tyr Ala Ser Leu Arg Thr Gly Val Thr Gln Asn Gly Gly Ser Asn Ala
                485                 490                 495

Cys Lys Arg Gly Pro Asp Ser Gly Phe Gly Gly Ser Ile Gln Ile
            500                 505                 510

Ile Pro Lys Ser Ser Trp Ser Asn His Glu Ala Ser Ser Gly Val Ser
        515                 520                 525

Ser Pro Thr Ile Lys Arg Ser Tyr Asn Asn Thr Asn Gln Glu Asp Leu
530                 535                 540

Leu Val Leu Trp Gly Gly Gly Ser Asp Ala Glu Asn Ala Pro Gly
545                 550                 555                 560

Gly Pro Tyr Arg Leu Gly Thr Ser Gly Ser Cys Pro Asn Ala Thr Met
                565                 570                 575

Ala Trp Ala Val Pro Lys Asp Asn Asn Lys Asn Ala Thr Asn Pro Leu
            580                 585                 590

Thr

<210> SEQ ID NO 2
<211> LENGTH: 1785
<212> TYPE: DNA
<213> ORGANISM: Artificial sequence
<220> FEATURE:
<221> NAME/KEY: CDS
<223> OTHER INFORMATION: Codon-optimized for high expression in E.coli
      gene coding for fusion protein

<400> SEQUENCE: 2

```
atggcgcagg tgattaacac caacagcctg agcctgctga cccagaacaa cctgaacaaa    60
agccagagcg cgctgggcac cgcgattgaa cgcctgagca gcggcctgcg cattaacagc   120
gcgaaagatg atgcggcggg ccaggcgatt gcgaaccgct ttaccgcgaa cattaaaggc   180
ctgacccagc gagccgcaa cgcgaacgat ggcattagca ttgcgcagac caccgaaggc   240
gcgctgaacg aaattaacaa caacctgcag cgcgtgcgcg aactggcggt gcagagcgcg   300
aacagcacca acagccagag cgatctggat agcattcagg cggaaattac ccagcgcctg   360
aacgaaattg atcgcgtgag cggccagacc cagtttaacg gcgtgaaagt gctggcgcag   420
gataacaccc tgaccattca ggtgggcgcg aacgatggcg aaaccattga tattgatctg   480
aaacagatta acagccagac cctgggcctg gcggcggca gcggcggcgg cagcggcggc   540
ggcagcgcgg cgaccaccac cgaaaacccg ctgcagaaaa ttgatgcggc gctggcgcag   600 gtggatacc tgcgcagcga tctgggcgcg gtgcagaacc gctttaacag cgcgattacc   660
aacctgggca caccgtgaa caacctgacc agcgcgcgca gccgcattga agatagcgat   720
tatgcgaccg aagtgagcaa catgagccgc gcgcagattc tgcagcaggc gggcaccagc   780
gtgctggcgc aggcgaacca ggtgccgcag aacgtgctga gcctgctgcg cggcggcggc   840
agcattgcga ttcgcccgaa agtgcgcgat caggaaggcc gcatgaacta ttattggacc   900
ctggtggaac cgggcgataa aattaccttt gaagcgaccg gcaacctggt ggtgccgcgc   960
tatgcgtttg cgatggaacg caacgcgggc agcggcatta ttattagcga taccccgccg  1020
tataacgata aatttgataa actgtatatt tggggcgtgc atcatccgag caccgatagc  1080
gatcagacca gcctgcatca tcgcctgatt gaaaaaacca acgaaaaatt tcatcagatt  1140
gaaaaagaat ttagcgaagt ggaacatcat tatgatcatg atgtgtatcg cgatgaagcg  1200
ctgaacaacc gctttcagat taaaggcgtg gaactgaaaa gcggctatac cattggcacc  1260
accattgcga ccagccgcgg cgtgggcacc ctgcagacca aaaacaccat tacctttatg  1320
acccagatga gccgcacctt taccacccgc agcgattata gcctgggcat tatgcagcgc  1380
agcctgggcg gcggcagccg cagcaaagcg tttagcaact gctatccgta tgatgtgccg  1440
gattatgcga gcctgcgcac cggcgtgacc cagaacggcg gcagcaacgc gtgcaaacgc  1500
ggcccggata gcggctttgg cggcggcagc attcagatta ttccgaaaag cagctggagc  1560
aaccatgaag cgagcagcgg cgtgagcagc ccgaccatta acgcagcta taacaacacc  1620 aaccaggaag atctgctggt gctgtgggc ggcggcggca gcgatgcgga aaacgcgccg  1680 ggcggccgt atcgcctggg caccagcggc agctgcccga acgcgaccat ggcgtgggcg  1740
gtgccgaaag ataacaacaa aaacgcgacc aacccgctga cctaa             1785
```